(12) United States Patent
Johnson

(10) Patent No.: US 10,376,390 B1
(45) Date of Patent: Aug. 13, 2019

(54) PROSTHETIC LIMB KIT AND METHOD OF MANUFACTURE

(71) Applicant: Phillip W. Johnson, Narrows, VA (US)

(72) Inventor: Phillip W. Johnson, Narrows, VA (US)

(*) Notice: Subject to any disclaimer, the term of this patent is extended or adjusted under 35 U.S.C. 154(b) by 83 days.

(21) Appl. No.: 15/613,045

(22) Filed: Jun. 2, 2017

Related U.S. Application Data

(60) Provisional application No. 62/344,954, filed on Jun. 2, 2016.

(51) Int. Cl.
*A61F 2/50* (2006.01)
*A61F 2/76* (2006.01)
*A61F 2/78* (2006.01)
*A61F 2/80* (2006.01)

(52) U.S. Cl.
CPC .............. *A61F 2/76* (2013.01); *A61F 2/5044* (2013.01); *A61F 2/78* (2013.01); *A61F 2/7812* (2013.01); *A61F 2/80* (2013.01); *A61F 2002/785* (2013.01); *A61F 2002/7818* (2013.01)

(58) Field of Classification Search
CPC ...... A61F 2/5044; A61F 2/5046; A61F 2/601; A61F 2/76; A61F 2002/5052; A61F 2002/5053; A61F 2002/5055; A61F 2002/7605; A61F 2002/761
See application file for complete search history.

(56) References Cited

U.S. PATENT DOCUMENTS

| 41,934 | A | 3/1864 | Monroe | |
|---|---|---|---|---|
| 1,153,532 | A | 9/1915 | Apgar | |
| 2,696,011 | A | 12/1954 | Galdik | |
| 3,461,464 | A * | 8/1969 | Lindgren | A61F 2/60 403/118 |
| 4,312,080 | A * | 1/1982 | Staats | A61F 2/76 623/27 |
| 4,459,709 | A | 7/1984 | Leal et al. | |
| 4,911,709 | A * | 3/1990 | Marlow | A61F 2/644 623/39 |
| 5,133,777 | A * | 7/1992 | Arbogast | A61F 2/60 264/DIG. 30 |
| 5,228,164 | A * | 7/1993 | Graf | A43D 1/022 12/133 R |
| 5,724,714 | A | 3/1998 | Love | |
| 5,888,231 | A | 3/1999 | Sandvig et al. | |
| 6,508,842 | B1 | 1/2003 | Caspers | |
| 6,793,682 | B1 | 9/2004 | Mantelmacher | |
| 7,883,547 | B2 | 2/2011 | Mantelmacher | |

(Continued)

OTHER PUBLICATIONS

Techform. Material Safety Data Sheet. Ossur. Jan. 2011.*

(Continued)

*Primary Examiner* — Thomas Sweet
*Assistant Examiner* — Christie L Bahena
(74) *Attorney, Agent, or Firm* — Winston & Strawn LLP

(57) ABSTRACT

A prosthetic limb is made from a portable kit that is of relatively low cost and easy to assemble and custom fit to a person in need so that the person can wear the prosthetic immediately, without having to wait for the prosthetic to be manufactured off-site. The embodiments include a below the knee device and an above the knee device that includes an artificial knee. The improved prosthetic is suited for replacing a missing leg but can also be adapted to replace another body part such as an arm, hand or foot.

19 Claims, 11 Drawing Sheets

(56) References Cited

U.S. PATENT DOCUMENTS

| | | | | |
|---|---|---|---|---|
| 2004/0153168 A1* | 8/2004 | Childress | ............... | A61F 2/66 623/55 |
| 2007/0055383 A1* | 3/2007 | King | ............... | A61F 2/68 623/34 |
| 2010/0114331 A1* | 5/2010 | Mantelmacher | ............... | A61F 2/60 623/36 |
| 2010/0304205 A1* | 12/2010 | Jo | ............... | H01G 9/02 429/144 |
| 2014/0277584 A1* | 9/2014 | Hurley | ............... | A61F 2/80 623/33 |

OTHER PUBLICATIONS

Ossur. Modular Socket System-Direct Lamination. 2015.*
SPS PVA Bag. SPS Website. Date verified by the wayback machine Mar. 7, 2016.*
OssurYT. Screen shot from YouTube Video: Ossur Presents: Modular Socket System. YouTube. Aug. 22, 2011.*
D-Rev, ReMotion Knee, http://d-rev.org/projects/mobility/, retrieved Jun. 2, 2017 (4 pages).
Travis Williams, "Nonprofit Hope to Walk helping injured get back on their feet," The Roanoke Times, Mar. 26, 2016 (9 pages); http://www.roanoke.com/news/local/blacksburg/nonprofit-hope-to-walk-helping-injured-get-back-on-their/article_1ae3a731-e6bf-5bb6-aa9e-09d2273d7bc2.html.
Kristi OConnor, "Johnson City man creates affordable prosthetics," News 5 WCYB, Sep. 30, 2015 (6 pages); http://www.wcyb.com/health/johnson-city-man-creates-affordable-prosthetics/14352346.

* cited by examiner

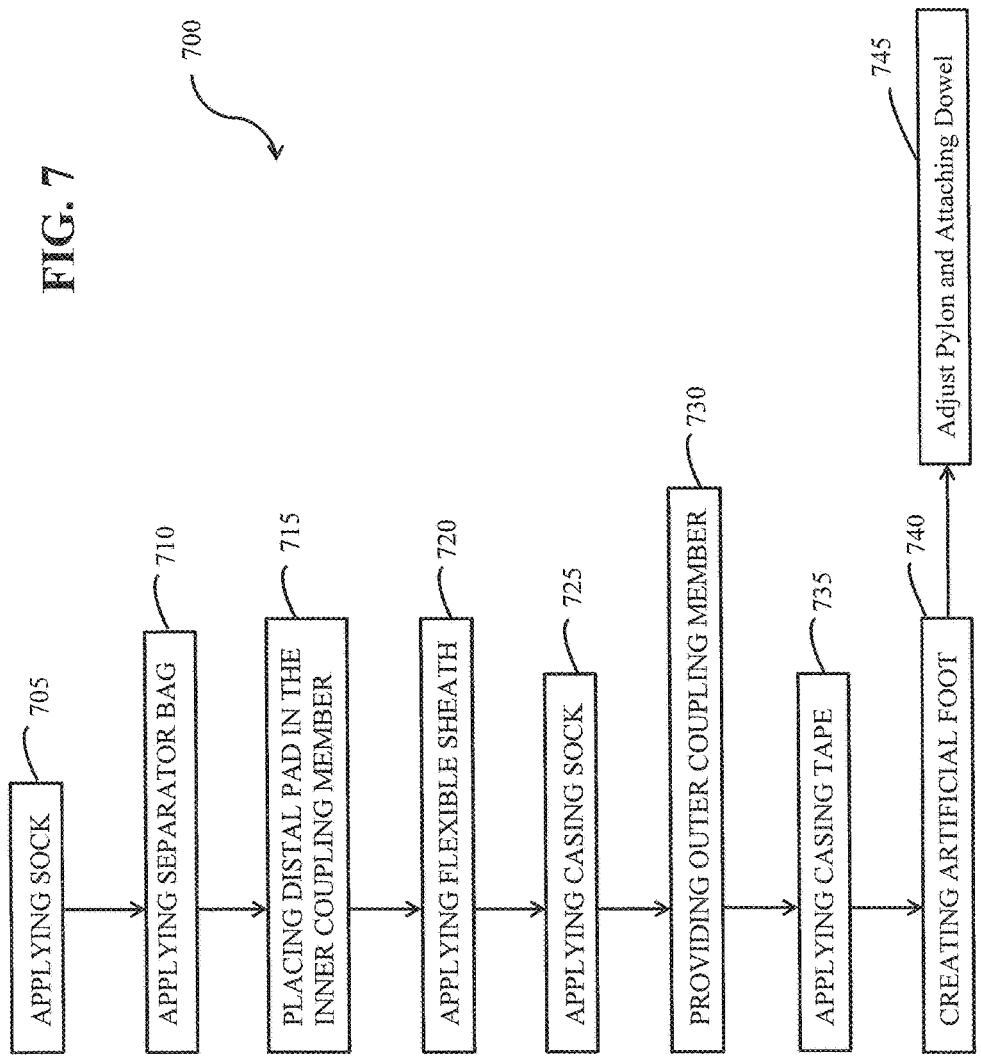

PROSTHETIC LIMB KIT AND METHOD OF MANUFACTURE

RELATED APPLICATIONS

This application claims the benefit of U.S. Provisional Application 62/344,954, filed Jun. 2, 2016, the entirety of which is herein incorporated by reference.

FIELD OF THE INVENTION

The field of the invention relates to a prosthetic limb and method of making the prosthetic limb. In particular, the invention provides a portable kit that is of relatively low cost and easy to assemble and custom fit to a person in need so that the person can wear the prosthetic immediately, without having to wait for the prosthetic to be manufactured off-site.

DESCRIPTION OF THE RELATED ART

Throughout history, humans have lost limbs as a result of accidents, military combat, illnesses, and hereditary defects. In the United States, approximately 2 million people have had amputation of an arm or leg. As medical science improved, prosthetic limbs became available. Prosthetics are artificial devices that replace missing body parts.

Prosthetics have been manufactured out of metals, plastics, wood, leather, carbon fiber, polycarbonates, resins, and laminates. To achieve a customized and comfortable fit, health care providers typically saw an amputee, took measurements, and made a cast. The cast was then sent offsite to a manufacturing facility, where a socket would be created, often out of a synthetic material. The socket would be mailed to the prosthetic provider. At that point, the amputee would return to the prosthetic provider to be fit into the socket. However, during the long time between the initial making of the cast and the delivery of the socket, the amputee's limb stump has changed in shape, size and/or dimension through, for example, atrophy, weight loss, weight gain, or other reasons. If the socket did not fit the amputee well, the provider could make minor adjustments to the socket. But if the socket required a substantial change, a new cast has to be made and the time-consuming process of manufacturing a new socket would have to be repeated, after which there is no guarantee that the revised socket would fit yet again. Therefore, there is a need for a prosthetic that can be built to custom fit an amputee so the amputee can walk out on a working prosthetic without having to wait for the prosthetic to be manufactured off-site.

SUMMARY OF THE INVENTION

As an aspect of the novel kit and method described herein, an example embodiment is a prosthetic limb that is provided in a kit with easy to assemble features so that it can be created on a person in need quickly and efficiently. Thus, the person can be fitted with the prosthetic limb at their location, without having to forward measurements to a different location where the prosthetic would be manufactured. The improved prosthetic is suited for a missing body part such as an arm, leg, hand, or foot.

The present invention now provides a kit for preparing a prosthetic leg for a person having a missing portion of a leg and a remaining stump. The kit comprises a plurality of components including a sock adapted to fit over the person's stump; a separator bag adapted to cover the sock and the person's stump; a distal pad configured and dimensioned for placement below the person's stump to provide cushioning; an inner coupling member having a concave lower surface and an upper inner surface forming an opening configured and dimensioned to receive at least part of the distal pad therein and to hold the distal pad in position below the person's stump; a flexible sheath having a closed end adapted to receive the inner coupling member and distal pad therein and an open end which allows the sheath to be extended over the separator bag and sock to hold the inner coupling member and the distal pad against the person's stump; a casting sock comprising a fabric containing a water activated settable material that, after activation, is adapted to fit over the flexible sheath, the inner coupling member, the distal pad, and at least part of the separator bag and the sock when those components are in position on the person's stump; an outer coupling member having a lower surface that includes a socket having an opening, and an upper surface configured to receive the concave lower surface of the inner coupling member and being at least partially conformable about the inner coupling member; a casting tape comprising a fabric containing a water activated settable material and provided in a length or lengths that, after activation, are sufficient for attaching the outer coupling member to the person's stump while also covering the flexible sheath, the inner coupling member, the distal pad, and at least part of the separator bag and sock when those components are in position on the person's stump; a wooden dowel and a pylon comprising a plastic hollow tube configured to receive the wooden dowel, each of the wooden dowel and the pylon having a length that is adjustable to provide an overall length for the prosthetic leg to conform to the length needed for the person; components for forming an artificial foot comprising a plurality of shapeable members, one of which includes a hole for accommodating the pylon; and an adhesive for attaching the foot components together, for attaching the pylon or the wooden dowel to the hole of the foot component and to the socket opening of the outer coupling member, and for attaching the outer coupling member to the casting sock. In some embodiments, the kit may further comprise an artificial knee joint that is operatively associated with the pylon to provide knee movement to the prosthesis when constructed.

Another embodiment of the invention is a method for preparing a prosthetic leg from the kit for a person having a missing portion of a leg and a remaining stump, which comprises applying the sock over the person's stump; applying the separator bag over the sock and the person's stump; placing the distal pad below the person's stump; placing an inner coupling member below the distal pad to receive at least part of the distal pad therein and to hold the distal pad in position below the person's stump; applying the flexible sheath with the closed end placed around the inner coupling member and distal pad and with the open end extending the sheath over the separator bag and sock to hold those components against the person's stump; activating the casting sock by immersion in water and applying the activated casting sock to the flexible sheath; providing the upper surface of the outer coupling member beneath the closed end of the flexible sheath with the upper surface receiving the concave lower surface of the inner coupling member; conforming the upper surface of the outer coupling member at least partially about the distal pad; activating the casting tape by immersion in water; attaching the outer coupling member to the person's stump by wrapping the activated casting tape around the outer coupling member while also covering the flexible sheath, the inner coupling member, the distal pad, and at least part of the separator bag and sock when those components are in position on the person's stump; cutting the pylon to an appropriate length so that the prosthetic leg provides the correct height for the person; shaping the artificial foot components; adhesively attaching the shaped components of the artificial foot together to form the artificial foot; and adhesively attaching one end of the pylon to the socket opening of the outer coupling member and the other end of the pylon to the hole in the foot component of the artificial foot. When the kit further comprises an artificial knee, the pylon is cut with a saw or knife to receive the artificial knee and to position the knee at a correct anatomical location for the person.

Other kits, methods, features and advantages of the invention will be or will become apparent to one with skill in the art upon examination of the following figures and detailed description. It is intended that all such additional systems, methods, features and advantages be included within this description, be within the scope of the invention.

BRIEF DESCRIPTION OF THE DRAWINGS

Preferred features of the invention are now provided by the appended drawings figures, wherein:

FIG. 7 depicts an illustrative flow chart for the method of preparing a prosthetic leg from the prosthetic kit in accordance with some embodiments of the present invention.

Figure 1:
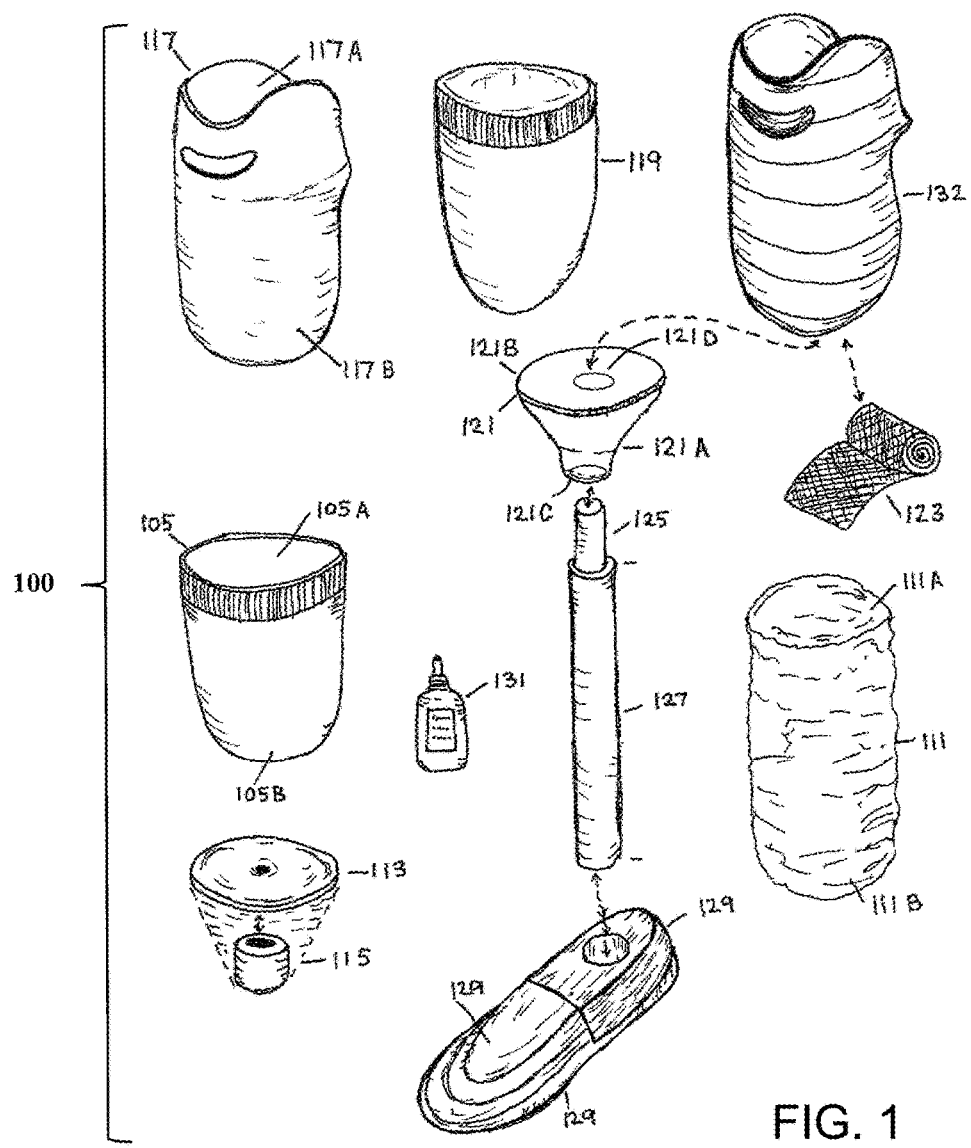
FIG. 1 depicts the components of a below the knee prosthetic leg kit according to the present invention.

The components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes is illustrated schematically rather than literally or precisely.

DETAILED DESCRIPTION OF THE INVENTION

The disclosed embodiments are for a kit for preparing a prosthetic limb and a method of making the prosthetic limb using the kit. The prosthetic limb can be made directly on a person in need, and by enabling a same day fit, the prosthetic limb contributes to improving the lifestyle of the person in need much sooner than by conventional manufacture, at a much lower cost. The size of the kit makes it transportable and thus serves the needs of amputees who are located in remote geographies or potentially even at the site of the amputation, such as in a war zone. In addition, the prosthetic can be created inexpensively. The invention is not limited to the below-described embodiments, but the invention can cover appropriate changes to the embodiments.

Turning now to the drawings, FIG. 1 depicts an illustrative prosthetic kit 100, which in this particularly preferred embodiment, is a kit for preparing a prosthetic leg. The kit 100 is designed for a person having a missing portion of a leg and a remaining stump. The kit 100 may comprise a plurality of components, including a sock 105, a separator bag 111, a distal pad 113, an inner coupler 115, a flexible sheath 117, a casting sock, 119, an outer coupler 121, a casting tape 123, a dowel 125, a pylon 127, components for forming an artificial foot 129, and an adhesive 131. Each of the plurality of components is low-cost and is made from low-cost materials and/or manufactured at low-cost. Low-cost may refer to materials able to be purchased inexpensively from generally available materials that can be tailored or conformed to the person in need using readily available and simple manufacturing tools or machines. Thus, the kit allows the preparation of the prosthetic leg at relatively low cost in just about any location. It also is particularly useful for persons in low income or poverty areas. The prosthetic leg prepared from the kit 100 is substantially less expensive compared to prostheses currently in the market which may cost between $5,000 and $50,000. The kit 100 generally costs less than $50, and the prosthetic leg prepared from the kit 100 by a health care professional would cost than less $200. Therefore, the prosthetic leg prepared from the kit 100 costs less than 1% to 5% of an average-cost prosthesis in the current market. The prosthetic leg is also simple to create such that it is built by a layperson, e.g., a family member or a friend, after reading the preparation steps and instruction details provided in the kit as described herein. The kits can also be provided at no cost by being donated to certain impoverished or war torn areas. In those situations, the prosthetic leg would be provided at an even lower cost or even at no cost to person that would otherwise not be able to obtain one.

For preparing the prosthetic leg, the sock 105 is first placed on the person's stump. The sock 105 directly touches the person's stump and provides some buffer between the skin and the remaining components, just like a sock worn on a foot provides cushioning to shoes which are worn on the foot. The sock 105 is typically a fabric sock that may made of cotton, wool, nylon, acrylic, polyester, olefins (such as polypropylene), spandex, linen, or any combination thereof. The fabric sock may also be made of other materials that provide comfort to the person's stump. The sock 105 has an open end 105a and a closed end 105b, and the open end 105a and the closed end 105b are typically the opposite ends of the sock 105.

The separator bag 111 is adapted to cover the sock 105 and the person's stump to provide a flexible barrier to the additional components that are to be added. The sock 105 receives the separator bag 111 from the closed end 105b. The separator bag 111 has a size or volume sufficient to cover the area on the sock 105 where the subsequently applied casting sock 119 and casting tape 122 will be applied. The separator bag 111 has an open end 111a and a closed end 111b, and a longitudinal length (from the open end 111a to the closed end 111b) that is longer than that of the casting tape 119. The separator bag 111 is put on the sock 105 from the closed end 105b toward the open end 105a through the open end 111a. The open end 111a has a diameter that is larger than that of the tip 105b. The open end 111a and the closed end 111b are two opposite ends of the separator bag 111. The separator bag 111 is preferably made of a waterproof material, such as polyurethane, polyamide, polyester, polyolefin (e.g., polyethylene and polypropylene), fluoropolymer, or any combination thereof. Other materials and combinations having similar characteristics may also be used. The separator bag 111 prevents the settable material of the casting sock 119 and/or the casting tape 123 and water from soaking the sock 105 or contacting the person's stump. The separator bag 111, for example, is conveniently a plastic tubular bag.

The distal pad 113 is configured and dimensioned for placement below the person's stump to provide cushioning. The distal pad 113 is configured to have a shape and/or structure that conforms or matches the shape of the person's stump. The distal pad 113 is dimensioned to have a size that fits below the person's stump and is typically a foam or gel material of a polyurethane, polyethylene, polyester, polyvinylchloride (PVC), silicone, rubber, or any combination thereof. Other materials and combinations having similar characteristics may also be used. The distal pad 113 is made to be softer or more resilient compared to the inner coupling member 115 to absorb shock and vibration and to provide comfort.

Figure 2:
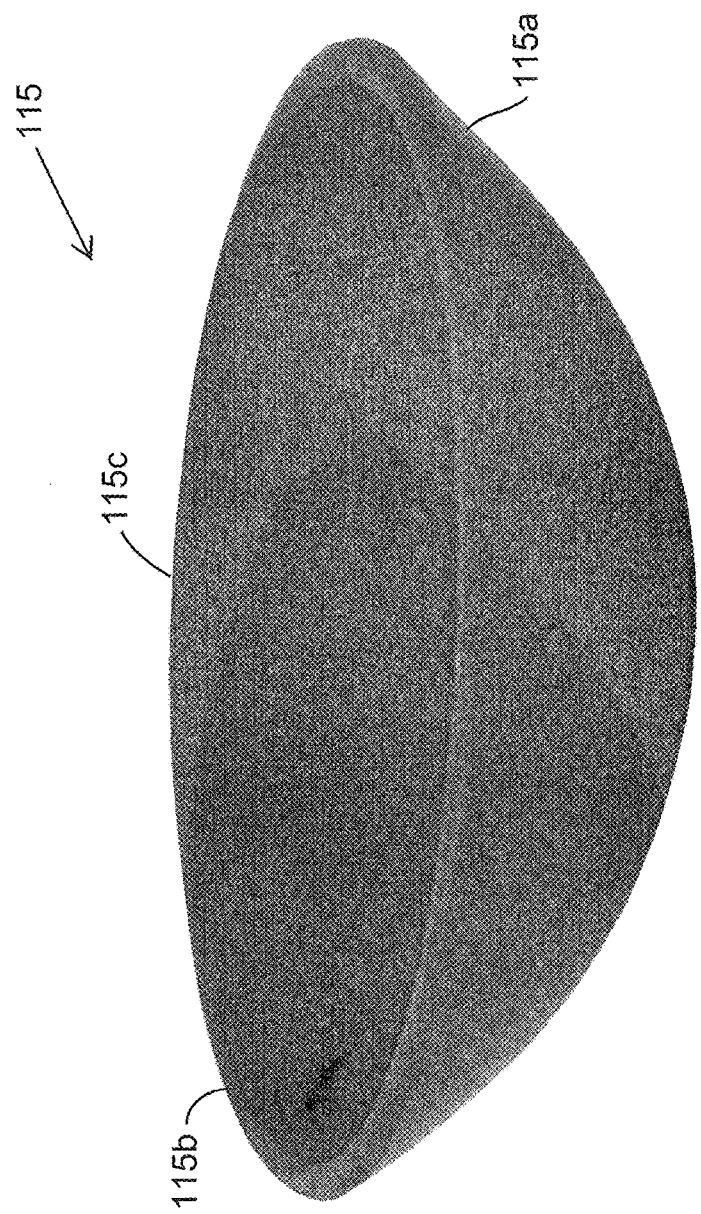
FIG. 2 depicts an illustrative inner coupling member in accordance with some embodiments with of the present invention.

FIG. 2 depicts an illustrative inner coupling member 115. The inner coupling member 115 has a concave lower surface 115a and an upper inner surface 115b. The upper inner surface 115b may form an opening 115c configured and dimensioned to receive at least part of the distal pad 113 and to hold the distal pad 113 in position below the person's stump. The opening 115c is configured to have a shape and/or structure that conforms or matches the shape and/or structure of the distal pad 113. The opening 115c is dimensioned to have a diameter or a depth that a portion of the distal pad 113 or the entire distal pad 113 is placed within the opening 115c. The inner coupling member 115 is preferably made of a plastic material such as polyvinyl chloride (PVC) or polypropylene, but it may also be made of the same material as the distal pad 113 or as the outer coupling member 121. Typically, however, the inner coupling member 115 is harder or less resilient compared to the distal pad 113 to provide protection to the distal pad 113 and the person's stump.

Figure 3:
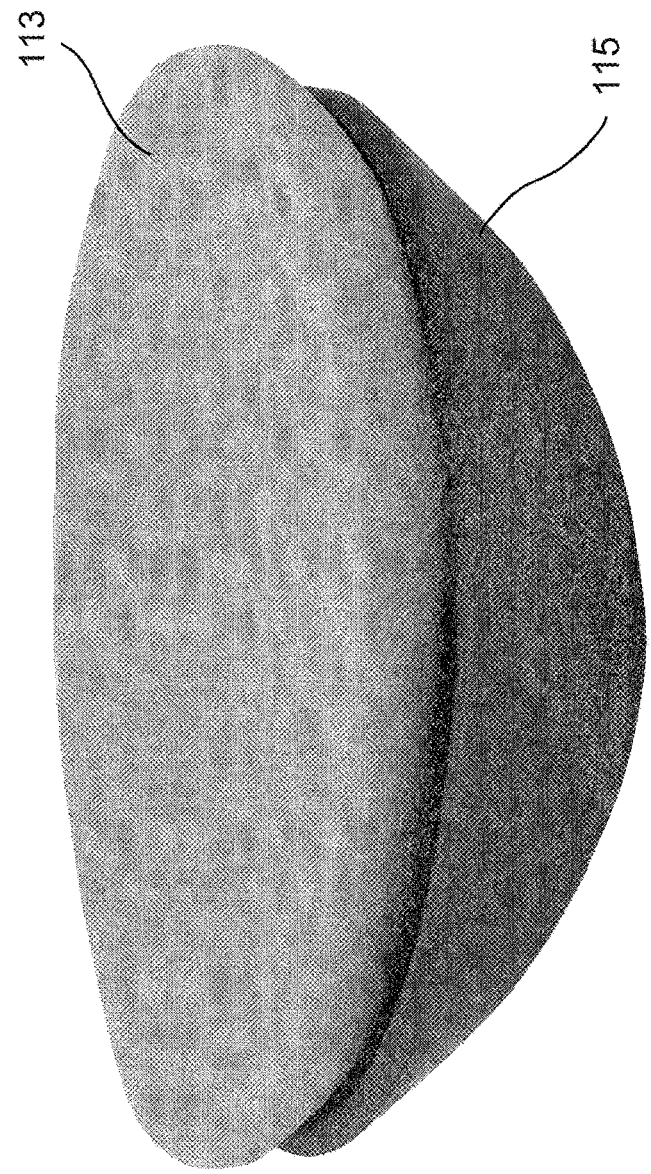
FIG. 3 depicts an illustrative inner coupling member receiving an illustrative distal pad in accordance with some embodiments of the present invention.

FIG. 3 depicts the inner coupling member 115 receiving the distal pad 113. The distal pad 113 may similarly have a concave lower surface and an upper inner surface, and the inner coupling member 115 may receive the distal pad 113 in a direction such that the concave lower surface of the distal pad 113 enters the opening 115c of the inner coupling member 115 first and contacts the upper inner surface 111b of the inner coupling member 115. The distal pad 113 may be larger or smaller than the inner coupling member 115 but generally they are essentially the same size.

Referring back to FIG. 1, the flexible sheath 117 is adapted to hold the inner coupling member 115 and the distal pad 113 against the person's stump. The flexible sheath 117 has an open end 117a adapted to receive the inner coupling member 115 and the distal pad 113 and a closed end 117b adapted to hold the inner coupling member 115 and the distal pad 113. The open end 117a may also allow the flexible sheath 117 to be extended over the separator bag and the sock 105 (hence the word "flexible") to hold the inner coupling member 115 and the distal pad 113 against the person's stump. The open end 117a may receive the inner coupling member 115 and the distal pad 113 with the inner coupling member 115 entering first. In particular, it is the concave lower surface 115a of the inner coupling member 115 that enters first. The closed end 117b may hold the inner coupling member 115 and the distal pad 113 with the inner coupling member 115 contacting the closed end 117b. In particular, it is the concave lower surface 115a of the inner coupling member 115 that contacts the closed end 117b. The flexible sheath 117 may be made of the same material as the sock 105 or of a different material. The flexible sheath 117 is preferably made of rubber or an elastomeric material or of another material that has similar flexibility characteristics. The flexible sheath 117 is made to elastically hold the separator bag 111 with the inner coupling member 115 and distal pad 113 therein tightly upon the sock 115. Tighter may refer to being harder to be removed from a person's stump or foot compared to the sock 105. Tightly refers to the situation that the person wearing the flexible sheath 117 feels that the flexible sheath 117 exerts more pressure on the person's stump or foot compared to the sock 105. The flexible sheath 117, for example, is a flexible synthetic stocking or expandable tube.

The casting sock 119 may comprise a fabric containing a water activated settable material. The fabric is made of the same material as the sock 105 or a different fabric material that is sufficiently porous to hold the settable material. The casting sock 119 is preferably made of polyester. The water activated settable material may comprise resin such as polyurethane resin, polyester resin, polyisocyanate resin, epoxy resin, plaster, or the like. The water activated settable material is preferably polyurethane resin. The casting sock 119 is activated by providing water to it. In one embodiment, the casting sock 119 is simply immersed in water for activation. Once activated, the casting sock 119 is applied to fit over the inner coupling member 115, the distal pad 113, and at least part of the flexible sheath 117, the separator bag 111, and the sock 105 when those components are in position with the person's stump. When the casting sock 119 is provided as a roll, after activation, the tape is unrolled and wrapped around the other components to attach them together to form an upper portion 132 of the prosthetic leg. The water activated settable material may cure within minutes once activated which hardens the casting sock 119. The water activated settable material may also be considered as a water-curable material. The casting sock 119, for example, is a casting sock manufactured by STS.

Figure 4:
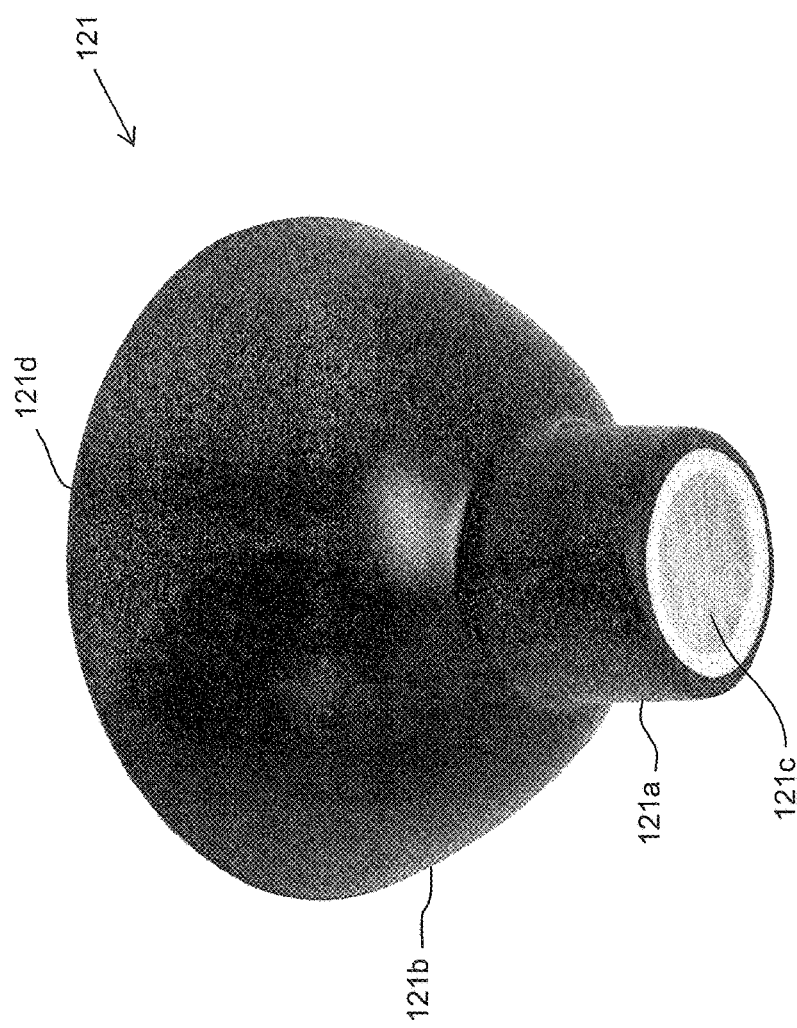
FIGS. 4 and 5 depict illustrative outer coupling members in accordance with some embodiments of the present invention.
Figure 5:
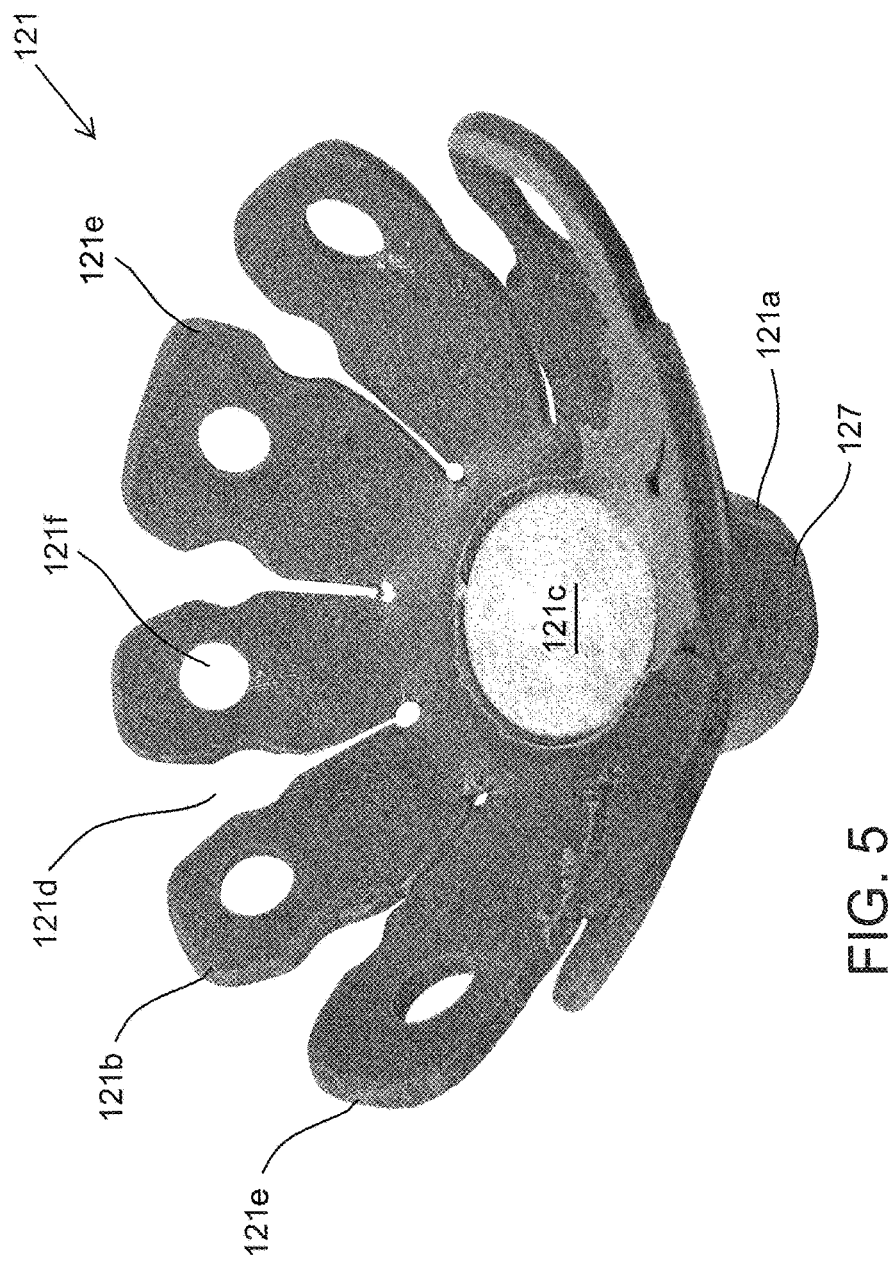

FIGS. 1, 4, and 5 depicts illustrative outer coupling members 115. The outer coupling member 115 has a form as shown in FIG. 4 or FIG. 5. In either form, the outer coupling member 115 has a lower surface 121a and an upper surface 121b. The lower surface 121a includes a socket 121c that is configured and dimensioned to receive a dowel 125 or other component that forms the pylon 127. The upper surface 121b forms a concave opening 121d that is configured and dimensioned to receive the person's stump. The socket 121c has a diameter or circumference that is smaller than that of the opening 121d. The outer coupling members 115 generally has an opening 121d with an approximately three-inch diameter and a socket 121c having an approximately 1⅛ inch diameter The outer coupling member 115 is preferably made of a material comprising a nontoxic thermosetting material or nontoxic heat shrinkable material such as polyvinyl chloride (PVC), polypropylene, polyethylene, terephthalates, polymethacrylate, polycarbonate, polystyrene, or the like. Thus, the outer coupling member 115 is shrinkable at least as to the upper surface 121b so that when heat is applied it can shrink and to conform to and about the inner coupling member 115 and the person's stump. In particular, the upper surface 121b or the opening 121d is at least partially conformable about the concave lower surface 115a of the inner coupling member 115. After heating, the upper surface 121b or the opening 121d engages the other components. In some embodiments, the upper surface 121b or the opening 121d may already fit the person's stump prior to heating in which case heating is not necessary. In this case, however, heating could be applied to further tighten the components. Configurations and dimensions used for the outer coupling member are similar to those described with respect to other components.

The outer coupling member 115 in FIG. 4 is modified to have a structure as shown in FIG. 5. The upper surface 121b of the outer coupling member 115 in FIG. 4 is formed with a plurality of petals 121e and a hole 121f in each of the petals 121e. Each petal 121e is heated individually and the heated petal 121e is adjusted to fit the diverse shape of the person's stump. The person's stump at this point is already protected by the flexible sheath 117, the inner coupling member 115, the distal pad 113, the separator bag 111, and the sock 105 and thus is not in direct physical contact with the heated petals 121e. The hole 121f is provided to facilitate adjustment since the petal 121e may expand in size or deform as it is heated. The kit 100 may include either or both outer coupling members 115.

Referring back to FIG. 1, the casting tape 123 may also comprise a fabric containing a water activated settable material. The fabric is made of fiberglass or another fabric material. The water activated settable material is made with a material similar to the water activated settable material of the casting sock 119. Once activated, the casting tape 123 is applied to wrap at least part of the outer coupling member 121 to the upper portion of the prosthesis that is already formed. The water activated settable material cures within minutes once activated which hardens the casting tape 123. The casting tape 123 provides additional force to hold the outer coupling member 121 and the other components together. The casting tape 123 may come in different width such as two inch, four inch, etc. The casting tape 123, for example, is a premium casting tape manufactured by Techform.

The dowel 125 and the pylon 127 each has a length that is adjustable to provide an overall length for the prosthetic leg to conform the length needed for the person receiving the prosthetic leg. The dowel 125 and the pylon 127 each may come with a length that is longer the missing portion of the leg (or be supplied at the longest length that would be reasonable expected to be used) and is reduced to conform the length needed for the person (or to the same length as the person in need's healthy leg). The dowel 125 and the pylon 127 has the same or different length before or after they are adjusted. The dowel 125 is made of wood or plastic and the pylon 127 is made of plastic. The pylon 127 may comprise a plastic pipe such as a PVC sprinkler or electrical conduit pipe which is readily available. Examples of such a pipe may include, but not limited to, Silver Line PVC 1120 and PVC schedule 40 pipe. The pylon 127 and the dowel 125 has the same or different cross-sectional shape. The pylon 127 typically comprises a hollow plastic tube configured to snugly receive dowel 125 therein. The dowel 125 gives strength and rigidity to the pylon 127 to prevent the pylon 127 from buckling or snapping under the weight of the person once the dowel 125 is inserted into the pylon 127. The dowel 125 is adjusted to be longer than the pylon 127 so that the dowel 125 protrudes from one or both open ends of the pylon 127. The length of the pylon can then be adjusted by a knife, a blade, a saw, or other cutting tool that is readily available to the length needed to properly size the length of the prosthetic leg.

In some embodiments, the kit 100 may comprise two dowels 125 shorter than the pylon 127 so that when each is inserted to each open end of the pylon 127, each dowel 125 or both dowels 125 do not extend through the entire length of the pylon 127. The portion between the dowels 125 in the pylon 127 may remain hollow.

Figure 6:
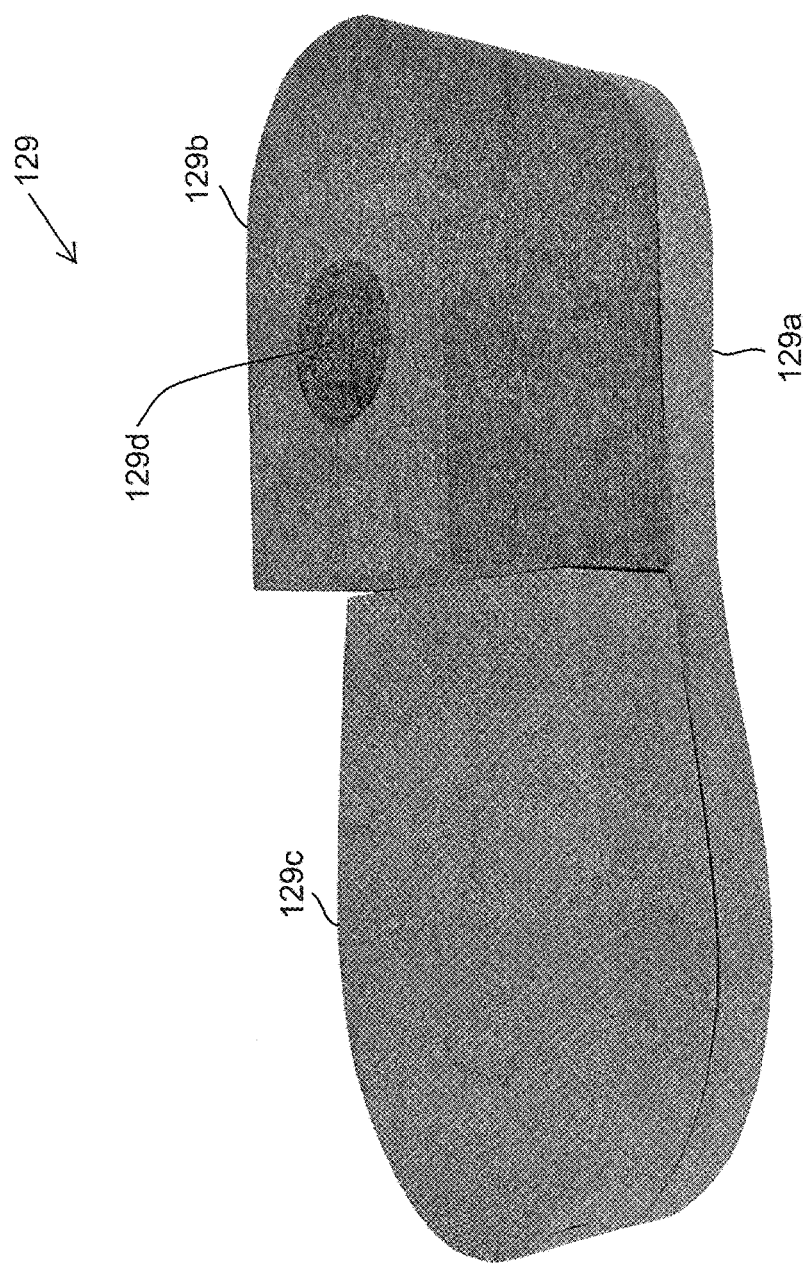
FIG. 6 depicts illustrative components for an artificial foot in accordance with some embodiments of the present invention.

FIG. 6 depicts illustrative components for forming an artificial foot 129. The components may comprise a bottom sole 129a, a solid piece of hard material 129b (or block 129b), and a top sole 129c. The block 129b and the top sole 129c are positioned on the same surface on the bottom sole 129a. The block 129b may include a hole 129d for accommodating the pylon 127 or the dowel 125. The hole 129d is located at about two inches from the junction of the block 129b and the top sole 129c. The components are made of rubber, plastic, wood, or crepe, and are easily adjusted to the appropriate final size and shape by a knife, a blade, a saw, or other cutting tool so that the artificial foot 129 can support the person's weight and is stable to support walking. Preferably, the bottom sole 129a is made of rubber, the block 129b is made of wood, and the top sole is made of crepe. Adjustment may also be made to the hole 129d. The components are referred to as adjustable or shapeable members. The bottom sole 129a has a shape resembling a person's foot or a shoe before or after the adjustment. The block 129b placed on the bottom sole 129a has a height in a direction toward the pylon 127 that is higher than the height of the top sole 129c and the bottom sole 129a in the same direction. The same height of the top sole 129c is also higher than the same height of the bottom sole 120c to provide stability and prevent warping or deformation of the bottom sole 129a. The top sole 129a may also have a weight that is heavier than the weight of the corresponding portion of the bottom sole 129a under the top sole 129a to gain the same benefits. The top sole 129c is adjusted or shaped to cover the remaining area of the surface that is not covered by the block 129b. These components are attached together by adhesive 131 to create an artificial foot. The artificial foot can be configured to serve as either a right foot or a left foot thus providing versatility to the kit for use to provide either a right or left prosthetic leg. The components are supplied with one size or the artificial foot is built with one size that typically fits most persons. The artificial foot is described as a SACH foot (solid ankle cushions heel) or Johnson foot.

Referring back to FIG. 1, adhesive 131 may comprise any suitable material such as Neoprene, natural rubber, synthetic rubber, epoxy resin, polyurethane, polyacrylate, polysulfide, cement, and the like. Adhesive is applied to attach any of the components together. Preferably, adhesive 131 is applied to attach the outer coupling member 121 and the pylon 127 or the dowel 125, the artificial foot and the pylon 127 or the dowel 125, the outer coupling member 121 and the person's stump, the distal pad 113 and the inner coupling member 115, and the components for forming the artificial foot 129. Adhesive 131 may comprise multiple packages with each package containing a certain material suitable for attaching specific components together.

The kit 100 may further comprise one or more fork-straps for assisting in retaining the prosthetic leg upon the person's stump during use. The one or more fork-straps are preferably made of leather. The kit 100 may further comprise a cutting tool and a sander to adjust or shape the components in the kit 100. The kit 100 may further comprise one or more screws for securing the components in the kit 100 together. The kit 100 may further comprise other tools necessary for assembling the components in the kit 100. The components in the kit 100 may also come with a configuration and dimension such that they are assembled without any adjustment.

FIG. 7 depicts an illustrative flow chart for the method 700 preparing a prosthetic leg from the prosthetic kit. The entire process is performed quickly with approximately 55 minutes from start to finish. The entire process may also is performed completely on the site of the person in need without having the person in need traveling to a medical office and without sending any mold, part, or component of the prosthetic leg prepared during the process to a manufacturing site or a doctor's office. The components of the kit 100 are assembled by tools readily available such as tools that are sold in a hardware store or convenience store and that can be purchased without substantially delaying the preparation process (e.g., tools that are purchased or otherwise obtained on the spot without special ordering or delivery). The method 700 may commence with pulling the sock 105 over the person's stump (step 705). The separator bag 111 is then pulled over the sock 105 (step 710) to prevent the water activated settable material and water from soaking the sock 105. A portion of the distal pad 113 is placed in the inner coupling member 115 (step 715), especially with the concave lower surface of the distal pad 113 placed in or in contact with the upper inner surface 111b of the inner coupling member 115. The flexible sheath 720 is applied to hold the distal pad 113 and the inner coupling member 115 against the person's stump with upper inner surface of the distal pad 113 contacting the person's stump and the concave lower surface of the inner coupling member 115 contacting the closed end of the flexible sheath 720. The open end of the flexible sheath 720 may extend over the separator bag 111 and the sock 105 to hold those components against the person's stump.

The casting sock 119 is then dipped in water, preferably warm water, to activate its water activated settable material. In some embodiments, the casting sock 119 is dipped in water prior to step 705, 710, 715, or 720 while other steps are simultaneously performed. After activation, the casting sock 119 is applied to fit over the flexible sheath 117, the inner coupling member 115, the distal pad 113, and at least of the separator bag and the sock 105 (step 725). The casting sock 119 is applied in a manner to insure that non-air bubbles or voids are present between the casting sock 119 and the flexible sheath 117.

After the casting sock 119 cures, the outer coupling member 121 is provided to the casting sock 119 on the person's stump (step 730). In some embodiments, the cured casting sock 119 is removed from the person's stump and the subsequent components is applied on the removed casting sock 119. The upper inner surface 121a of the outer coupling member 121 is provided beneath the cured casting sock 119. Adhesive 131 is provided between the cured casting sock 119 and the upper inner surface 121a. The upper inner surface 121a or petals 121e are then heated to conform at least partially with the cured casting sock 119. The cured casting sock 119 or the cured casting sock 119 containing all the components applied before the cured casting sock 119 is referred to as a socket which forms the upper portion 132 of the prosthetic leg.

The casting tape 123 is then dipped in water, preferably warm water, to activate its water activated settable material. In some embodiments, the casting tape 123 is dipped in water prior to step 705, 710, 715, 720, or 730 while other steps are simultaneously performed. After activation, the casting sock 119 is wrapped around at least part of the outer coupling member 121 and at least part of the socket to provide additional force bonding the two components. The casting tape 123 is applied in a manner to insure that non air bubbles or voids are present between the casting tape 123 and the socket and between the casting tape 123 and the outer coupling member 121. The casting tape 123 is wrapped in a manner that has fewer wrinkles. Preferably, the casting tape 123 is wrapped in a "figure eight" manner. (Step. 735.)

Components for forming the artificial foot 129 are adjusted or shaped to provide support and provide stability to the person in need (step. 740). The adjusted or shaped components are joined together by adhesive 131 to create the artificial foot 129. The artificial foot 129 is coated with a waterproof material or a protective material to prolong the life of the artificial foot 129.

The pylon 127 and/or the dowel 125 are cut to the proper length for the person in need (step 745). The proper length may refer to the length of the person in need's healthy leg or the length of the missing portion. After cutting, the dowel 125 is inserted into the pylon 127. After inserting, one end of the pylon 127 and/or the dowel 125 is inserted into and attached to the outer coupling member 121 using adhesive 131 and another end of the pylon 127 and/or the dowel 125 is inserted into and attached to the hole 129d of the artificial foot 129 using adhesive 131. A screw is used to screw the dowel 127 inside the pylon 125 to the artificial foot 129. Moreover, a fork-strap is attached to the socket and is used for attaching the prosthetic leg to the person in need by buckling to the remaining limb or the person in need's body.

The person preparing the prosthesis may examine the fit, motion, and dimensions of the prosthetic leg for suitability to the person in need. As the person walks using the prosthetic, the preparing person may watch and examine the operation of the prosthetic on the person in need and make any minor adjustments to the prosthetic.

Figure 8A:
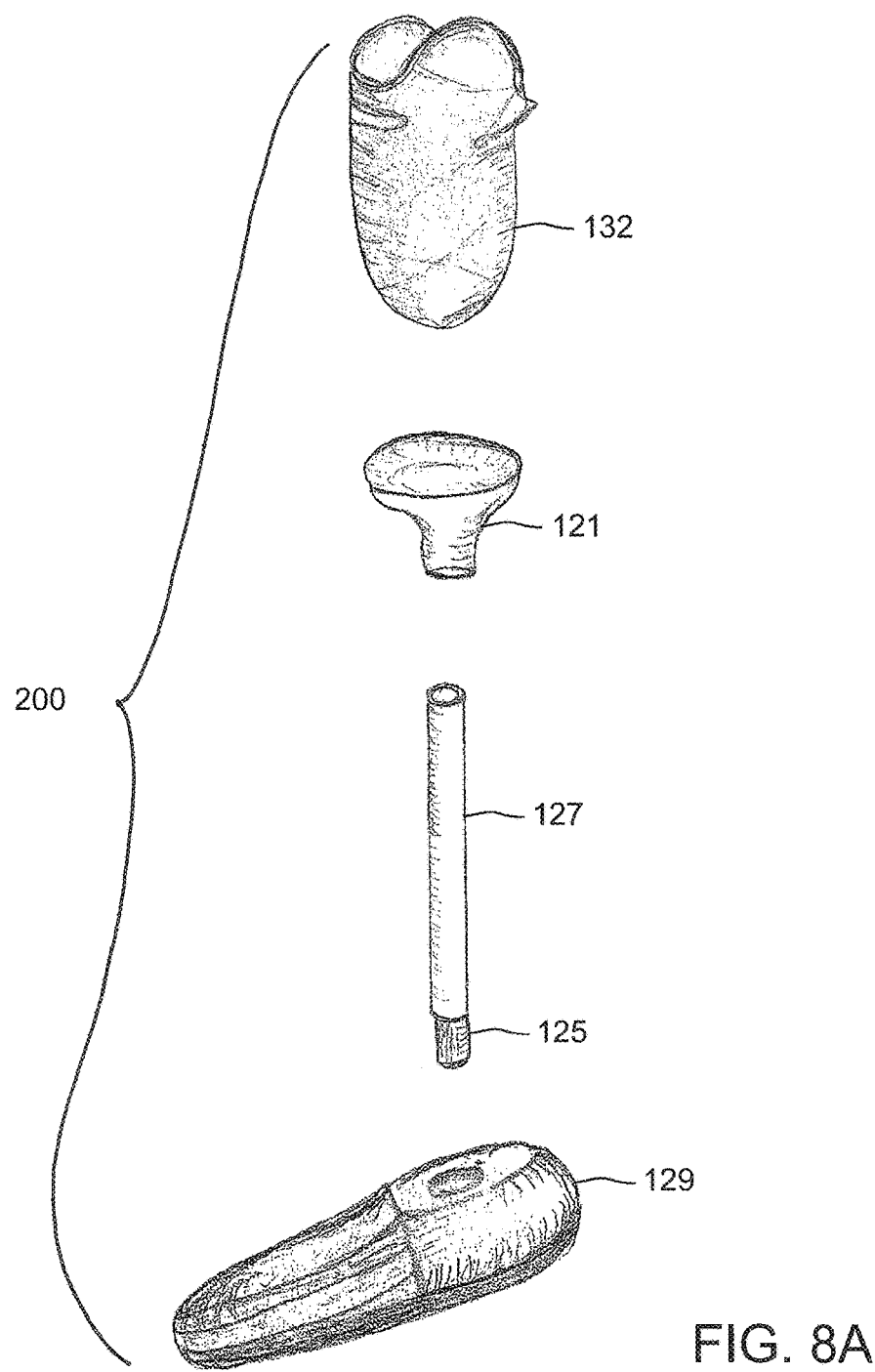
FIGS. 8A and 8B depict a prosthetic leg prepared from the kit of FIG. 1, with FIG. 8A being an exploded view and FIG. 8B being an assembled view of the prosthetic leg.
Figure 8B:
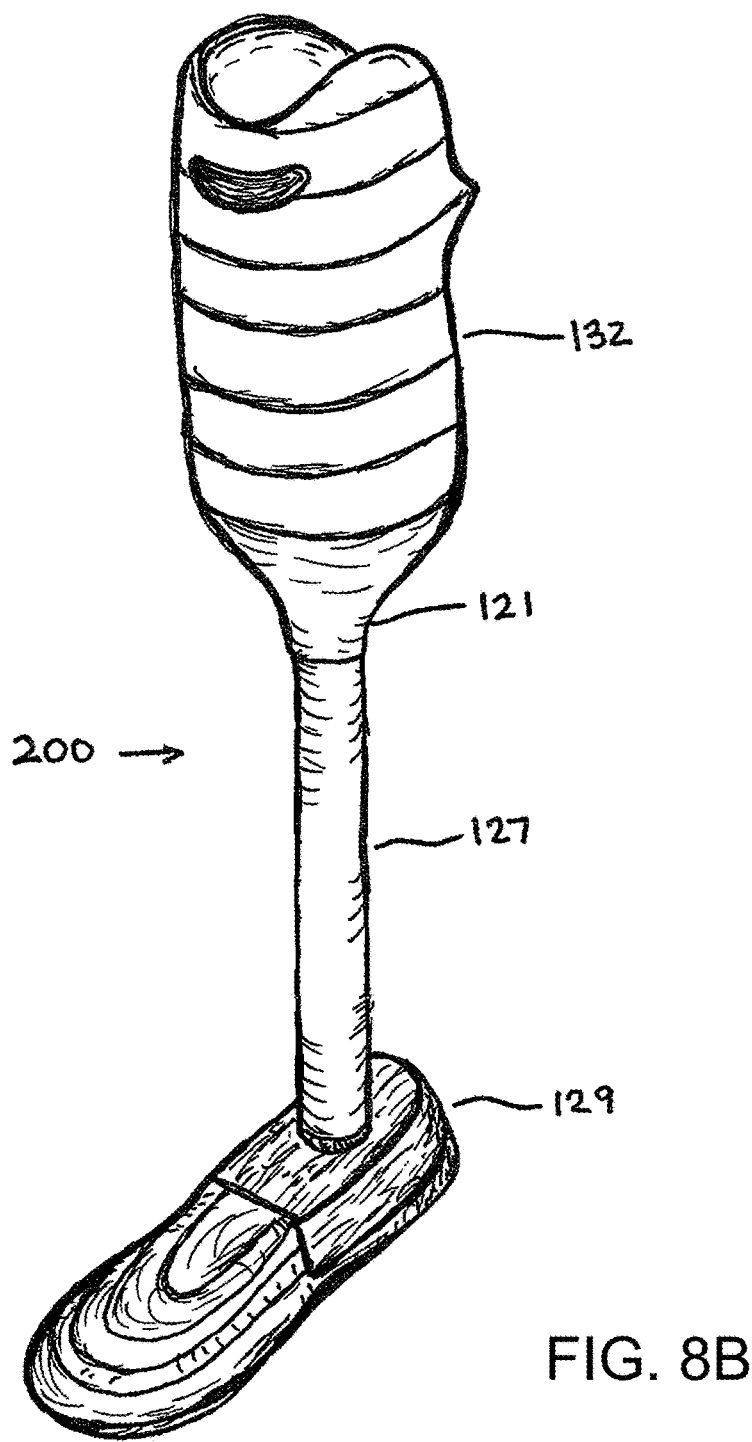

FIGS. 8A and 8B depict the prosthetic leg 200 prepared from the kit 100, with FIG. 8A being an exploded view and FIG. 8B being an assembled view. The prosthetic leg 200 may comprise socket 132 (which may comprise the cured casting sock or the cured casting sock containing all the components applied before the cured casting sock), outer coupling member 121, pylon 127, and artificial foot 129. The remaining components not shown in this figure are covered by one or more of these components.

The prostheses of the present invention can be used to replace a portion of the person's leg below the knee in which case the pylon is sized accordingly and the socket is attached to the persons stump. When the person has lost his or her leg above the knee, the pylon of the prosthesis can be provided in a longer length.

Figure 9:
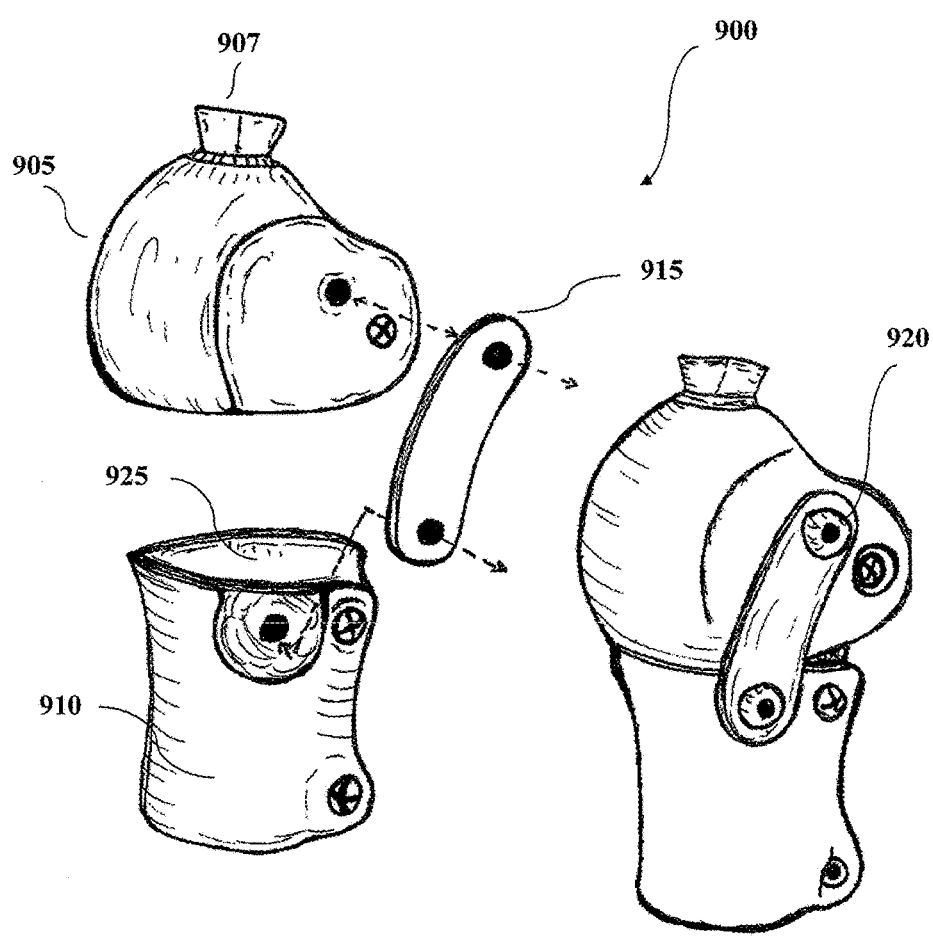
FIG. 9 depicts a commercially available artificial knee for use in the present invention.
Figure 10:
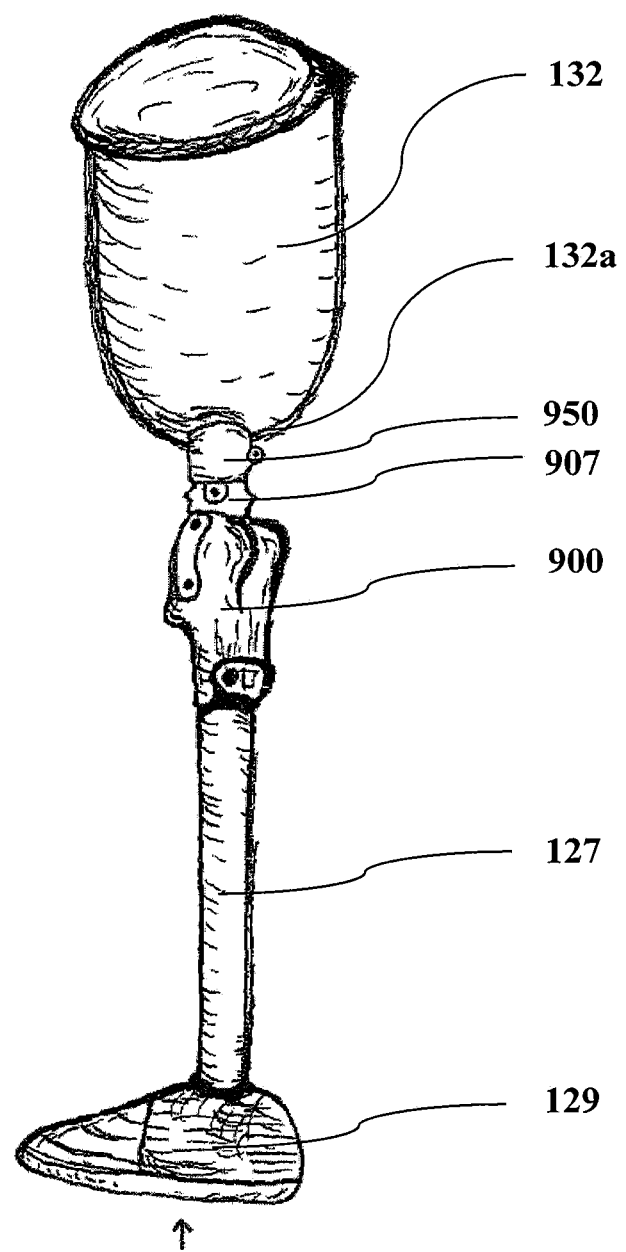
FIG. 10 illustrates a prosthesis for an artificial leg that includes the artificial knee of FIG. 9.

Persons who have lost a leg above the knee have also lost the articulation ability of the knee joint. Thus, in another embodiment of the invention, an articulating knee joint 900 as shown in FIGS. 9 and 10 is provided. This joint 900 is a commercially available low cost artificial knee that is known as the ReMotion Knee Joint (v3) which is available from D-Rev: Design Revolution, 695 Minnesota Street, San Francisco, Calif. 94107 (http://d-rev.org/projects/mobility/). The joint 900 includes an upper portion 905 having a protrusion 907, a lower portion 910, and a plate 920 connecting the upper portion 905 and the lower portion 910 in a manner such that the upper portion 905 is movable with respect to the lower portion 910 (or vice versa). For example, when force is exerted on the upper portion 905 or the protrusion 907, the upper portion 905 is rotated in a direction with the protrusion 907 moving toward the lower portion 910. When force is released, the upper portion 905 is rotated in another direction with the protrusion 907 moving away from the lower portion 910. The upper portion 905 and the lower portion 910 may be in physical contact without interfering their movement. The lower portion 910 includes an opening 925 on which the upper portion 905 is placed. The protrusion 907 may be a pyramid or a pyramid receiver. The plate 920 is connected to the upper portion 905 with a fastener (e.g., screw) and to the lower portion 910 with another fastener. The protrusion 907 includes a structure configured to fit or receive the coupling member or other type of connector 950. The structure and size of the protrusion 907 can be modified to fit or receive the coupling member or other type of connector 950. The other type of connector 950 may be a socket attachment plate with pyramid (or pyramid receiver) and through hole, a multi-prong adapter with pyramid (or pyramid receiver), a rotatable pyramid (or pyramid receiver), and the like.

The joint 900 is connected to the socket 132 from the tip 132a of the socket 132 and is situated in a location corresponding to the person's knee. The joint 900 is connected to the tip 132a via the coupling member or other types of connector 950. The distance between the tip 132a and the joint 900 can be adjusted by changing the length or structure of the protrusion 907, the coupling member, other type of connector 950, or a combination thereof so the location of the joint 900 can be customized for each individual. The pylon 127 is appropriately reduced in size and is connected to the joint 900 via the opening 925 of the lower portion 910. Another end of the pylon 127 is inserted into the artificial foot 129. The joint 900 and the connection discussed enable the person to utilize the prosthesis in the same manner as a normal knee which facilitates movement, motion and sitting. While this does add some cost to the replacement prosthesis, the advantage of having articulating knee movement provides a substantial benefit to the person in providing the ability to move as they did before loss of the leg and knee. Even so, the kit with the artificial knee generally costs less than $100, and the prosthetic leg and knee prepared from the kit by a health care professional would cost than less $300.

FIGS. 9 and 10 depict an illustrative artificial knee that can be used with the prosthetic leg. Other types of artificial knee may also be used with the prosthetic leg. Other types of artificial knee may be connected to the prosthetic leg via the same coupling member or connector used above or a different coupling member or connector configured to fit or receive that particular type of artificial knee.

As used herein, the term "the person's stump" may refer to the person's stump prior to any component is applied or after one or more components are applied to the person's stump. For example, the person's stump may refer to the person's stump covered by one or more of the sock, the separator bag, the distal pad, inner couple member, the flexible sheath, and/or the casting sock, depending on the progress of the method.

Although embodiments of the present invention illustrate a prosthetic in the form of a leg, they can be provided for a different body part such as an arm or other missing body parts for which a prosthetic is suitable. Many of the same materials and process steps are followed with of course appropriate adjustment for provided, e.g., a hand instead of a foot component, a ratcheted component for an elbow in the pylon, etc. Skilled artisans can understand how to adapt the invention disclosed herein for replacement of an arm instead of a leg and for that reason those embodiments are also contemplated by the present invention.

In the foregoing specification, the invention has been described with reference to specific embodiments thereof. It will, however, be evident that various modifications and changes is made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions. As another example, each feature of one embodiment can be mixed and matched with other features shown in other embodiments. Features and processes known to those of ordinary skill in the art of identification appliances may similarly be incorporated as desired. Additionally and obviously, features is added or subtracted as desired. Accordingly, the invention is not to be restricted.

What is claimed is:

1. A kit for preparing a prosthetic leg for a person having a missing portion of a leg and a remaining stump, the kit consisting of:

a sock adapted to fit over the person's stump;

a separator bag adapted to cover the sock and the person's stump, the separator bag having an open end and a closed end, the closed end having dimensions sufficient for covering the sock without exposing the sock;

a distal pad having smooth surfaces configured and dimensioned for placement below the person's stump to provide cushioning;

an inner coupling member having a concave lower surface and an upper inner surface forming an opening configured and dimensioned to receive at least part of the distal pad therein and to hold the distal pad in position below the person's stump;

a flexible sheath having a closed end adapted to receive the inner coupling member and distal pad therein and an open end which allows the sheath to be extended over the separator bag and sock to hold the inner coupling member and the distal pad against the person's stump;

a casting sock comprising a fabric containing a water activated settable material that, after activation, is adapted to fit over the flexible sheath, the inner coupling member, the distal pad, and at least part of the separator bag and the sock when those components are in position on the person's stump;

an outer coupling member having a lower surface that includes a socket having an opening, and an upper surface configured to receive the concave lower surface of the inner coupling member and being at least partially conformable about the inner coupling member;

a casting tape comprising a fabric containing a water activated settable material and provided in a length or lengths that, after activation, are sufficient for attaching the outer coupling member to the person's stump while also covering the flexible sheath, the inner coupling member, the distal pad, and at least part of the separator bag and sock when those components are in position on the person's stump;

a wooden dowel and a pylon comprising a plastic hollow tube configured to receive the wooden dowel, each of the wooden dowel and the pylon having a length that is adjustable to provide an overall length for the prosthetic leg to conform to the length needed for the person;

components for forming an artificial foot that can support a wearer's weight during use, with the artificial foot comprising a plurality of shapeable members, one of which includes a hole for accommodating the pylon; and an adhesive for attaching the foot components together, for attaching the pylon or the wooden dowel to the hole of the foot component and to the socket opening of the outer coupling member, and for attaching the outer coupling member to the casting sock and including strap members for assisting in retaining the prosthetic leg upon the person's stump during use.

2. The kit of claim 1, wherein the sock is a fabric sock.

3. The kit of claim 1, wherein the separator bag is made of a waterproof material that prevents the settable material of the casting sock, the casting tape, or both the casting sock and the casting tape from contacting the person's stump.

4. The kit of claim 3, wherein the waterproof material is polyurethane, polyamide, polyester, polyolefin, fluoropolymer, or any combination thereof.

5. The kit of claim 1, wherein the distal pad is made of a gel or foam material and wherein the flexible sheath is made of nylon.

6. The kit of claim 1, wherein the inner and outer coupling members are each made of plastic and the outer coupling member is made of a heat shrinkable material so that it can be tightly conformed to the inner coupling member and the distal pad.

7. The kit of claim 6, wherein an upper surface of the outer coupling member includes a plurality of petals that can be conformed to the inner coupling member and the distal pad.

8. The kit of claim 7, wherein the plurality of petals are made of a heat shrinkable material which upon heating can conform the petals to the inner coupling member and the distal pad.

9. The kit of claim 1, wherein the casting tape comprises fabric or fiberglass and the settable material comprises polyurethane resin.

10. The kit of claim 1, wherein the adhesive is made of Neoprene, natural rubber, synthetic rubber, epoxy resin, polyurethane, polyacrylate, polysulfide, cement.

11. The kit of claim 1, wherein the flexible sheath is tighter than the sock in elasticity and the distal pad is more resilient compared to the inner coupling member.

12. A kit for preparing a prosthetic leg for a person having a missing portion of a leg and a remaining stump, the kit consisting of:

a sock adapted to fit over the person's stump;

a separator bag adapted to cover the sock and the person's stump, the separator bag having an open end and a closed end, the closed end having dimensions sufficient for covering the sock without exposing the sock;

a distal pad having smooth surfaces configured and dimensioned for placement below the person's stump to provide cushioning;

an inner coupling member having a concave lower surface and an upper inner surface forming an opening configured and dimensioned to receive at least part of the distal pad therein and to hold the distal pad in position below the person's stump;

a flexible sheath having a closed end adapted to receive the inner coupling member and distal pad therein and an open end which allows the sheath to be extended over the separator bag and sock to hold the inner coupling member and the distal pad against the person's stump;

a casting sock comprising a fabric containing a water activated settable material that, after activation, is adapted to fit over the flexible sheath, the inner coupling member, the distal pad, and at least part of the separator bag and the sock when those components are in position on the person's stump;

an outer coupling member having a lower surface that includes a socket having an opening and an upper surface configured to receive the concave lower surface of the inner coupling member and being at least partially conformable about the inner coupling member;

a casting tape comprising a fabric containing a water activated settable material and provided in a length or lengths that, after activation, are sufficient for attaching the outer coupling member to the person's stump while also covering the flexible sheath, the inner coupling member;

the distal pad, and at least part of the separator bag and sock when those components are in position on the person's stump;

a wooden dowel and a pylon comprising a plastic hollow tube configured to receive the wooden dowel each of the wooden dowel and the pylon having a length that is adjustable to provide an overall length for the prosthetic leg to conform to the length needed for the person;

an artificial knee joint that is operatively associated with the pylon to provide knee movement to the prosthesis when constructed;

components for forming an artificial foot that can support a wearer's weight during use, with the artificial foot comprising a plurality of shapeable members, one of which includes a hole for accommodating the pylon; and an adhesive for attaching the foot components together, for attaching the pylon or the wooden dowel to the hole of the foot component and to the socket opening of the outer coupling member, and for attaching the outer coupling member to the casting sock.

13. A method for preparing a prosthetic leg for a person having a missing portion of a leg and a remaining stump, which comprises:

Providing a kit consisting of:

a sock adapted to fit over the person's stump;

a separator bag adapted to cover the sock and the person's stump, the separator bag having an open end and a closed end, the closed end having dimensions sufficient for covering the sock without exposing the sock;

a distal pad having smooth surfaces configured and dimensioned for placement below the person's stump to provide cushioning;

an inner coupling member having a concave lower surface and an upper inner surface forming an opening configured and dimensioned to receive at least part of the distal pad therein and to hold the distal pad in position below the person's stump;

a flexible sheath having a closed end adapted to receive the inner coupling member and distal pad therein and an open end which allows the sheath to be extended over the separator bag and sock to hold the inner coupling member and the distal pad against the person's stump;

a casting sock comprising a fabric containing a water activated settable material that, after activation, is adapted to fit over the flexible sheath, the inner coupling member, the distal pad, and at least part of the separator bag and the sock when those components are in position on the person's stump;

an outer coupling member having a lower surface that includes a socket having an opening, and an upper surface configured to receive the concave lower surface of the inner coupling member and being at least partially conformable about the inner coupling member;

a casting tape comprising a fabric containing a water activated settable material and provided in a length or lengths that, after activation, are sufficient for attaching the outer coupling member to the person's stump while also covering the flexible sheath, the inner coupling member, the distal pad, and at least part of the separator bag and sock when those components are in position on the person's stump;

a wooden dowel and a pylon comprising a plastic hollow tube configured to receive the wooden dowel, each of the wooden dowel and the pylon having a length that is adjustable to provide an overall length for the prosthetic leg to conform to the length needed for the person;

components for forming an artificial foot that can support a wearer's weight during use, with the artificial foot comprising a plurality of shapeable members, one of which includes a hole for accommodating the pylon; and an adhesive for attaching the foot components together, for attaching the pylon or the wooden dowel to the hole of the foot component and to the socket opening of the outer coupling member, and for attaching the outer coupling member to the casting sock and including strap members for assisting in retaining the prosthetic leg upon the person's stump during use;

applying the sock over the person's stump;

applying the separator bag over the sock and the person's stump;

placing the distal pad below the person's stump;

placing the inner coupling member below the distal pad to receive at least part of the distal pad therein and to hold the distal pad in position below the person's stump;

applying the flexible sheath with the closed end placed around the inner coupling member and distal pad and with the open end extending the sheath over the separator bag and sock to hold those components against the person's stump;

activating the casting sock by immersion in water and applying the activated casting sock to the flexible sheath;

providing the upper surface of the outer coupling member beneath the closed end of the flexible sheath with the upper surface receiving the concave lower surface of the inner coupling member;

conforming the upper surface of the outer coupling member at least partially about the distal pad;

activating the casting tape by immersion in water;

attaching the outer coupling member to the person's stump by wrapping the activated casting tape around the outer coupling member while also covering the flexible sheath, the inner coupling member, the distal pad, and at least part of the separator bag and sock when those components are in position on the person's stump;

cutting the pylon to an appropriate length so that the prosthetic leg provides the correct height for the person;

shaping the artificial foot components;

adhesively attaching the shaped components of the artificial foot together to form the artificial foot; and adhesively attaching one end of the pylon to the socket opening of the outer coupling member and the other end of the pylon to the hole in the foot component of the artificial foot.

14. The method of claim 13, wherein the first and second coupling members are each made of plastic and the second coupling member is at least partially made of a heat shrinkable material; and heating the second coupling member so that it can be tightly conformed to the inner coupling member and distal pad.

15. The method of claim 14, wherein the upper surface of the second coupling member includes spaced tab members that are made of a heat shrinkable plastic material that is conformed to the inner coupling member and distal pad by heating of the heat shrinkable plastic material.

16. The method of claim 14, wherein the kit further comprises an artificial knee and the pylon is cut with a saw or knife to receive the artificial knee and to position the knee at a correct anatomical location for the person.

17. The method of claim 13, wherein the tape is applied in a manner to ensure that no air bubbles or voids are present between the tape and the outer coupling member and between the tape and the casting sock.

18. The method of claim 13, wherein the casting sock is applied in a manner to insure that no air bubbles or voids are present so that the prosthesis is securely attached to the person's stump.

19. The method of claim 13, further comprising heating the upper surface of the outer coupling member to conform that member with the casting sock.

* * * * *